(12) United States Patent
Turner

(10) Patent No.: US 10,953,150 B2
(45) Date of Patent: Mar. 23, 2021

(54) CONTROL SYSTEM

(71) Applicant: Spectrum Medical Ltd., Gloucester (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 524 days.

(21) Appl. No.: 15/575,602

(22) PCT Filed: May 17, 2016

(86) PCT No.: PCT/GB2016/051415
§ 371 (c)(1),
(2) Date: Nov. 20, 2017

(87) PCT Pub. No.: WO2016/185197
PCT Pub. Date: Nov. 24, 2016

(65) Prior Publication Data
US 2018/0154061 A1   Jun. 7, 2018

(30) Foreign Application Priority Data

May 21, 2015   (GB) ...................................... 1508731
Sep. 15, 2015   (GB) ...................................... 1516331

(51) Int. Cl.
  *A61M 1/36*        (2006.01)
(52) U.S. Cl.
  CPC ........ *A61M 1/3624* (2013.01); *A61M 1/3627* (2013.01); *A61M 1/3666* (2013.01);
  (Continued)

(58) Field of Classification Search
  CPC .............. A61M 1/3624; A61M 1/3626; A61M 1/3627; A61M 1/3629; A61M 1/3632;
  (Continued)

(56) References Cited

U.S. PATENT DOCUMENTS 3,890,969 A   6/1975   Fischel
4,887,411 A   12/1989  Rondeau et al.
(Continued)

FOREIGN PATENT DOCUMENTS

CN    106659840 A    5/2017
EP    1 344 543      9/2003
(Continued)

OTHER PUBLICATIONS

European Patent Office, Examination Report for Application No. 16723496.2, dated Aug. 13, 2018, 4 pages.
(Continued)

*Primary Examiner* — Philip R Wiest
(74) *Attorney, Agent, or Firm* — Sunstein LLP

(57) ABSTRACT

A control system for controlling a quantity of blood in a blood reservoir (10) of a perfusion system supplied by a venous line (V), wherein a pump (20) circulates blood from the blood reservoir (10) through an outgoing line (A), comprises a venous flow sensor (22) to measure a venous blood flow rate, an outlet flow sensor (24) to measure an outgoing blood flow rate, and a controller to control the pump (20) to prevent the outgoing blood flow rate from exceeding the venous blood flow rate. Thereby, a decrease of blood in the blood reservoir (10) can be arrested.

17 Claims, 4 Drawing Sheets

(52) U.S. Cl.
CPC .............. *A61M 2205/3334* (2013.01); *A61M 2205/3341* (2013.01); *A61M 2205/3379* (2013.01)

(58) Field of Classification Search
CPC .............. A61M 1/3639; A61M 1/3663; A61M 2205/3334; A61M 2205/3341; A61M 2205/3379
See application file for complete search history.

(56) References Cited

U.S. PATENT DOCUMENTS

| | | | | |
|---|---|---|---|---|
| 2002/0085952 | A1* | 7/2002 | Ellingboe | A61M 1/3632 422/45 |
| 2008/0195022 | A1* | 8/2008 | Lucke | A61M 1/3627 604/4.01 |
| 2012/0130299 | A1 | 5/2012 | Knott et al. | |

FOREIGN PATENT DOCUMENTS

| | | |
|---|---|---|
| EP | 3167920 A1 | 8/2015 |
| EP | 3165246 A1 | 10/2017 |
| WO | WO 93/01858 | 2/1993 |
| WO | WO2012/141756 A2 | 10/2012 |
| WO | WO-2012141756 A2 * | 10/2012 .......... A61M 1/1698 |

OTHER PUBLICATIONS

European Patent Office, Examination Report for Application No. 16723496.2, dated Apr. 4, 2019, 6 pages.

United Kingdom Intellectual Property Office, Search Report—Application No. GB1508731.5, dated Dec. 1, 2005, 3 pages.

Violaine Pinta, Authorized officer European Patent Office, International Search Report—Application No. PCT/GB2016/051415, dated Aug. 1, 2016, together with the Written Opinion of the International Searching Authority, 9 pages.

Chinese Patent Office, Examination Report for Application No. 201680042345.0, dated Dec. 24, 2019, 9 pages.

* cited by examiner

CONTROL SYSTEM

FIELD OF THE INVENTION

The present invention relates to a system and method for managing, more specifically for controlling, an amount of blood in a blood reservoir of a perfusion system.

BACKGROUND

Extracorporeal perfusion is a process in which blood from a patient is circulated outside the patient's body and re-oxygenated to be returned to the patient. More specifically, venous (oxygen-reduced) blood which has been removed from a patient via a venous line is oxygenated by exposure to an oxygenation gas in an oxygenator for supply via an arterial line back to the patient as arterial blood.

The properties of the blood drawn from a patient may vary during perfusion. In particular, the flow rate and/or amounts of blood collected from a patient may vary. In order to maintain steady flow conditions in the oxygenator and/or through to other components, venous blood is collected in a blood reservoir, or venous reservoir, from where the blood is then drawn for subsequent processing (e.g., to undergo oxygenation in the oxygenator). Likewise, demand for blood from the reservoir varies.

The blood supply into the blood reservoir may vary constantly, and so the blood level in the blood reservoir may momentarily sink to levels that may be hazardous to a patient. For instance, too low a blood level in the blood reservoir may result in air bubbles being drawn into the blood. Such air bubbles may present a hazard if the blood is to be returned to the patient.

Blood reservoirs may conventionally comprise a blood level sensor. If the level of blood is too low, a signal is provided to an operator (e.g. a member of a surgical team operating on a patient) to stop the blood circulation away from the reservoir.

The present invention seeks to provide improved means for reducing the risks associated with a low blood level in a blood reservoir.

SUMMARY OF THE INVENTION

In accordance with a first aspect of the present invention, there is provided a control system for controlling a quantity of blood in a blood reservoir as defined in claim 1.

The control system is configured for use with a blood reservoir of a perfusion system in which the blood reservoir is supplied through a venous line and a pump is configured to circulate blood out of the blood reservoir through an outgoing line. The control system comprises a venous flow sensor configured to measure a venous flow rate of blood in the venous line, an outgoing flow sensor configured to measure an outgoing flow rate of blood in the outgoing line, and a controller. The controller is configured to receive as inputs the venous flow rate and the outgoing flow rate. The controller comprises decision logic permitting it to issue a signal to control the pump to prevent the outgoing flow rate from exceeding the venous flow rate so as to arrest a decrease of blood in the blood reservoir.

The venous line provides blood to the blood reservoir. Components located at the venous line can be assumed to be upstream of the blood reservoir. Likewise, the outgoing line transports blood from the blood reservoir. Components located at the outgoing line can be assumed to be downstream of the blood reservoir.

In an embodiment, the outgoing line is an arterial line and the outlet flow sensor is an arterial flow sensor. The arterial flow sensor is configured to measure as the outgoing flow rate an arterial flow rate of blood in the arterial line. In the embodiment, the controller prevents the arterial flow rate from exceeding the venous flow rate.

It will be understood that by providing a mechanism to maintain the outgoing (e.g., arterial) flow rate at and/or below the venous flow rate, the amount of blood entering the blood reservoir is equal to, or exceeds, respectively, the amount of blood drawn from the reservoir. Thereby, a mechanism is provided to maintain the quantity of blood in the blood reservoir above a minimum level. A mechanism to maintain the outgoing flow rate relative to the venous flow rate may be regarded as a closed loop control.

The outgoing (e.g., arterial) flow sensor and the venous flow sensor may continuously measure the flow rate. This improves the response time of the closed loop control.

The present invention allows a closed loop control to be implemented even though it may not be possible to control the venous blood flow rate. The closed loop control provides a more responsive mechanism to prevent a low blood level situation. A low blood level situation is undesirable because it may lead to air being sucked in with the blood that is withdrawn from the blood reservoir. The sucking in may cause air bubbles to be created in the blood. Air bubbles in the blood may pose a hazard to a patient if the blood is subsequently administered to the patient. Air bubbles in blood, if subsequently administered to a patient, may prolong patient post-operation recovery times, may be responsible for causing embolic ischemic events such as stroke, and even cause death. Also, air bubbles may interfere with blood measurements.

In an embodiment, the control system further comprises a blood quantity sensor system configured to generate a blood quantity output indicative of a quantity of blood in the blood reservoir. In the embodiment, the controller is configured to receive as a further input the blood quantity output, to determine whether the blood quantity output is below a first blood quantity threshold, and to control the pump to prevent the outgoing flow rate from exceeding the (incoming) venous flow rate while the quantity of blood is below the first blood quantity threshold in the blood reservoir.

It will be understood that a first blood quantity threshold is a threshold that is set according to operational needs. The first blood quantity threshold may be set to ensure a minimum amount of blood is maintained in the blood reservoir.

One reason for the varying blood flow into the blood reservoir is that blood may originate from multiple sources, e.g., from vents and/or suckers. Vents are connections directly to the heart of a patient, and for the purpose of the present specification vented blood is fed via a venous line into the blood reservoir. Suckers are blood salvage devices that collect blood as and when accumulated during surgery, and for the purpose of the present specification salvaged blood is fed via a salvage line into the blood reservoir. It will be understood that the present invention is not concerned with a method of obtaining blood from a patient. It will suffice to appreciate that the flow of blood into the blood reservoir may vary.

A reason for varying blood flow out of the blood reservoir is that outgoing blood may be drawn by a plurality of devices. The core component of a perfusion system is, typically, an oxygenator provided to oxygenate blood in the outgoing line. Blood from the outgoing line may also be drawn to supply a cardioplegia (heart-arresting) line, in which blood serves as a carrier fluid for the administration of a cardioplegic agent, or to supply a hemoconcentrator (device for removal of excess plasma liquid), for filter purge flows, oxygenator purge flows, and for blood sampling. Thus, even if the venous flow rate corresponds to the regular outgoing flow, temporary additional blood demand may lead to a reduction of the quantity of blood in the blood reservoir.

If the venous flow rate continues to remain lower than the outgoing flow rate and there is not sufficient blood flow from other sources, such as salvaged blood, into the blood reservoir, the quantity of blood in the blood reservoir may drop below the first blood quantity threshold. In that case, the closed loop control allows the outgoing flow rate to be maintained at and/or below the venous flow rate by preventing the outgoing flow rate from exceeding the venous flow rate, to arrest a further decrease in the quantity of blood in the blood reservoir.

In an embodiment, the blood quantity sensor system is configured to measure the quantity of blood based on the level of blood in the blood reservoir, the volume of blood in the blood reservoir, or the mass of blood in the blood reservoir.

The quantity of blood in the blood reservoir may be determined by a level sensor, or by measuring the volume or weight (mass) of blood in the blood reservoir. Conveniently, the thresholds are determined corresponding to the sensor output. E.g., a reference to a blood quantity threshold may be understood to be a reference to a blood level threshold if the sensor determines the quantity of blood by the blood level. Blood level sensors allow the quantity of blood to be determined without having to consider blood clotting. Likewise, the blood quantity threshold may be understood as a reference to a threshold of the blood volume, or mass, respectively, if the sensor determines the quantity of blood by volume, or mass, respectively.

The sensors may be non-contact sensors. Non-contact sensors allow a determination of the quantity of blood to be made without coming into physical contact with the blood.

Non-contact sensors facilitate the taking of frequent or continuous measurements. Also, non-contact sensors reduce the risk of contamination.

Exemplary non-contact sensors include light-based sensors or ultrasonic sensors.

In an embodiment, the controller is configured to determine whether the blood quantity output is below a second blood quantity threshold, and to stop the pump to stop the outgoing (e.g., arterial) flow while the quantity of blood is below the second blood quantity threshold.

If, for any reason, the maintaining of the outgoing flow rate at and/or below the venous flow rate does not suffice to stop the decrease of blood in the blood reservoir, a second blood quantity threshold may be monitored as a hard stop.

In an embodiment, the controller is configured to stop the outgoing (e.g., arterial) flow by gradually reducing the pump throughput to zero.

This prevents too abrupt a stop of the flow in the outgoing line. Blood flowing at speed downstream of the roller pump has some inertia. Abruptly stopping the flow, e.g. from a flow rate in the region of 5 litres per minute to zero, may cause a momentary spike of a negative pressure gradient of the blood moving through the oxygenator (downstream of the just stopped pump), pulling air across the oxygenator fibres into the blood phase. The risk of this occurring is reduced by gradually reducing the flow rate to zero.

For instance, the controller may be configured to reduce the flow over a pre-determined time interval, e.g., over 1 to 2 seconds, to zero flow. The controller may be configured to reduce the flow rate at a pre-determined rate of change, e.g., by 2 litres per minute per second. This will reduce a flow rate from 5 litres per minute to zero in 2.5 seconds.

It will be understood that the time permissible from a controller starting to gradually reduce the pump throughput until the stop of outgoing flow depends on the second blood quantity threshold. I.e., if the second blood quantity threshold is higher, a more gradual stopping of the outflow may be appropriate. In that case, more time can be allowed for stopping the outgoing flow gradually.

The second blood quantity threshold is understood to be lower than the first blood quantity threshold. As such, the second blood quantity threshold may correspond to a lower quantity of blood in the blood reservoir than the first blood quantity threshold.

In an embodiment, the blood quantity sensor system comprises a blood quantity sensor capable of monitoring the first blood quantity threshold and the second blood quantity threshold. As such, the blood quantity sensor system may comprise only a single sensor.

In an embodiment, the blood quantity sensor system comprises a first blood quantity sensor for monitoring the first blood quantity threshold and a second blood quantity sensor for monitoring the second blood quantity threshold.

Using separate sensors for the thresholds may facilitate the installation and/or the calibration of the thresholds for different blood reservoir geometries.

In an embodiment, the controller is configured to control the pump independently of the venous flow rate if the quantity of blood is above the first blood quantity threshold.

After a period of low blood flow into the blood reservoir, the blood flow may increase, e.g., because more blood is being salvaged from a patient, or because the outgoing flow rate is maintained below the venous flow rate. Thereby, the quantity of blood in the blood reservoir may increase above the first blood quantity threshold. In that case, it may be safe to operate at outgoing flow rates independently of the venous flow rate, even if this causes a decrease of blood in the blood reservoir, as long as the quantity of blood is not below the first blood quantity threshold.

In embodiments, the blood reservoir is further supplied by one or more salvage lines, and a blood flow through the one or more salvage lines is not considered in the determination by the controller as to whether or not the outgoing (e.g., arterial) flow rate exceeds the venous flow rate.

Salvaged blood may be fed in to the reservoir via one or more salvage lines. The blood flow through the salvage line is assumed to be less steady than the blood flow of vented blood through the venous line. The present Applicant has appreciated that a reliable feedback loop to prevent a low blood level situation can be achieved by monitoring the flow rate in the venous line.

The venous flow sensor may be configured for attachment on the venous line.

In an embodiment, the venous flow sensor is configured for attachment on an inlet of the blood reservoir.

Positioning the venous flow sensor close to the inlet of the blood reservoir improves the accuracy of the venous flow measurement for the purposes of the closed loop control.

In an embodiment, the venous flow sensor is integral with the blood reservoir.

An integral flow sensor facilitates the installation and setup of the control system.

In an embodiment, the control system further comprises a blood oxygenator downstream of the blood reservoir.

The closed loop control of the present invention improves the usage of an oxygenator, because the amount of blood drawn from the blood reservoir in a low blood situation is limited by the venous flow rate. This provides a more balanced control than, e.g., a manual switching off of the pump.

In an embodiment, the blood oxygenator is located downstream of the pump.

In an embodiment, the control system comprises two or more outgoing flow sensors, each outgoing flow sensor to measure an outgoing flow rate at a different location of the outgoing line.

In an embodiment, two or more outgoing flow sensors are in series and the controller is configured to receive as inputs the outgoing flow rates of the outgoing flow sensors in series, and wherein the controller is configured to issue the signal to control the pump if any of the outgoing flow rates exceeds the venous flow rate.

In an embodiment, two or more outgoing flow sensors are in parallel and the controller is configured to receive as inputs the outgoing flow rates of the parallel outgoing flow sensors, to determine a cumulative outgoing flow rate as the sum of the outgoing flow rates, and wherein the controller is configured to issue the signal to control the pump if the cumulative outgoing flow rate exceeds the venous flow rate.

In systems with two or more outgoing lines, each outgoing line may be provided with an outgoing flow sensor. A pump may be provided in each outgoing line. The total flow out of the blood reservoir can be determined by the cumulative outgoing flow rates. In that case, the controller may reduce the pump speed until the cumulative outgoing flow rate no longer exceeds the venous flow rate.

Depending on the tubing configuration, several flow sensors may be provided to measure the flow rate at different locations. For instance, a perfusion system may comprise two outgoing lines, such as an oxygenation line and a cardioplegia line, each to separately draw blood from a blood reservoir outlet. In the cardioplegia line, an outgoing flow sensor may be positioned near the blood reservoir outlet. In the oxygenation line, an outgoing flow sensor may be positioned near the blood reservoir outlet, i.e., upstream of any blood-diverting components, and another outgoing flow sensor may be positioned downstream of the oxygenator, to measure the flow rate of the arterialised blood. The outgoing flow sensors in the oxygenation line are in series. The flow sensor in the cardioplegia line operates in parallel to the outgoing flow sensors in the oxygenation line. The decision logic of the control system allows providing that the cumulative flow rate of the cardioplegia line and the larger of the two flow rates in the oxygenation line is not exceeding the venous flow rate.

The outgoing flow sensor may be configured for attachment on an outlet of the pump. This helps to ensure that blood is circulated by the pump into the oxygenator only if there is enough blood in the blood reservoir.

In an embodiment, at least one outgoing flow sensor is located downstream of the blood oxygenator.

The oxygenator may affect the flow rate, and so a more accurate measurement of the actual outgoing flow rate may be obtained by measuring the blood after it passed the oxygenator. This location is particularly suitable if it can be assumed that blood is diverted only downstream of the oxygenator, and/or that any unaccounted losses occur predominantly downstream of the oxygenator.

In an embodiment, at least one outgoing flow sensor is located downstream of any blood-diverting component.

By blood-diverting component, any components are meant that permit blood to be drawn from the outgoing line. This includes purge lines, cardioplegia lines, blood-sampling offtakes, or losses. A blood-diverting component reduces the flow rate in the outgoing line. Thus, a more accurate measurement of the actual flow rate may be obtained by measuring the flow rate downstream of any blood-diverting components.

In an embodiment, at least one outgoing flow sensor is located upstream of any blood-diverting components.

This allows the outgoing flow rate to be determined before any blood flow reduction. This improves the reliability of the feedback loop to prevent a decrease of the amount of blood in the blood reservoir. At least one outgoing flow sensor may be located upstream of the oxygenator.

In an embodiment, at least one outgoing flow sensor is located upstream of the pump.

The outgoing flow sensor may be configured for attachment on an inlet of the pump. This helps to ensure that the outgoing flow is measured independently of the number and type of any blood-diverting devices downstream of the pump.

In an embodiment, at least one outgoing flow sensor is configured for attachment on an outlet of the blood reservoir.

The closer the flow sensor is located at the blood reservoir, the smaller the risk that any unaccounted blood losses affect the measured flow. This helps to ensure that the outgoing flow is measured independently of the number and type of any blood-diverting devices downstream of the blood reservoir. Positioning the outgoing flow sensor close to the outlet of the blood reservoir improves the accuracy of the outgoing flow measurement for the purposes of the closed loop control.

In an embodiment, at least one outgoing flow sensor is integral with the blood reservoir.

This facilitates the installation and setup of the control system.

In accordance with a second aspect of the present invention, there is provided a method of controlling a quantity of blood in a blood reservoir as defined in claim 24.

In the method, the blood reservoir is intended for use in a perfusion system in which the blood reservoir is supplied through a venous line and a pump is configured to circulate blood out of the blood reservoir through an outgoing line.

The method comprises the steps of using a venous flow sensor to measure a venous flow rate of blood in the venous line, using an outgoing flow sensor to measure an outgoing flow rate of blood in the outgoing line, determining whether or not the outgoing flow rate exceeds the venous flow rate, and operating the pump so as to prevent the outgoing flow rate from exceeding the venous flow rate so as to arrest a decrease of blood in the blood reservoir.

In an embodiment, the outgoing line is an arterial line and the outlet flow sensor is an arterial flow sensor. In the embodiment, the method comprises using the arterial flow sensor to measure as the outgoing flow rate an arterial flow rate of blood in the arterial line, determining whether or not the arterial flow rate exceeds the venous flow rate, and operating the pump so as to prevent the arterial flow rate from exceeding the venous flow rate.

The outgoing (e.g., arterial) flow rate is prevented from exceeding the venous flow rate by operating the pump so as to maintain the outgoing flow rate at and/or below the venous flow rate.

In an embodiment, the method further comprises the steps of using a sensor to measure a blood quantity output indicative of a quantity of blood in the blood reservoir, determining whether the blood quantity output is below a first blood quantity threshold, and operating the pump so as to prevent the outgoing (e.g., arterial) flow rate from exceeding the venous flow rate while the quantity of blood is below the first blood quantity threshold.

In an embodiment, the method further comprises the steps of determining whether the quantity of blood is below a second blood quantity threshold, and stopping the pump to stop the outgoing (e.g., arterial) flow while the quantity of blood is below the second blood quantity threshold.

In an embodiment, stopping the pump comprises gradually reducing pump throughput to zero to stop the outgoing flow.

In an embodiment, the method further comprises the step of controlling the pump independently of the venous flow rate if the quantity of blood is above the first blood quantity threshold.

In an embodiment, the method further comprises the step of positioning the venous flow sensor at an inlet of the blood reservoir.

In an embodiment, the method further comprises the step of passing the blood from the blood reservoir through a blood oxygenator.

In an embodiment, the method further comprises using two or more outgoing flow sensors, and using each outgoing flow sensor to measure an outgoing flow rate at a different location of the outgoing line.

In an embodiment, the method further comprises positioning two or more outgoing flow sensors in series, determining the outgoing flow rates of each of the outgoing flow sensors in series, and operating the pump if any of the outgoing flow rates exceeds the venous flow rate.

In an embodiment, the method further comprises positioning two or more outgoing flow sensors in parallel, determining a cumulative outgoing flow rate as the sum of the outgoing flow rates, and operating the pump if the cumulative outgoing flow rate exceeds the venous flow rate.

In an embodiment, the method further comprises the step of measuring the outgoing flow rate downstream of the blood oxygenator.

In an embodiment, the method further comprises the step of measuring the outgoing flow rate downstream of any blood-diverting component, downstream of the pump, and/or at an outlet of the pump.

In an embodiment, the method further comprises the step of measuring the outgoing flow rate upstream of any blood-diverting component, upstream of the pump, at an outlet of the blood reservoir, and/or at an inlet of the pump.

DESCRIPTION OF THE FIGURES

Exemplary embodiments of the invention will now be described with reference to the Figures, in which.

DESCRIPTION

Figure 1:
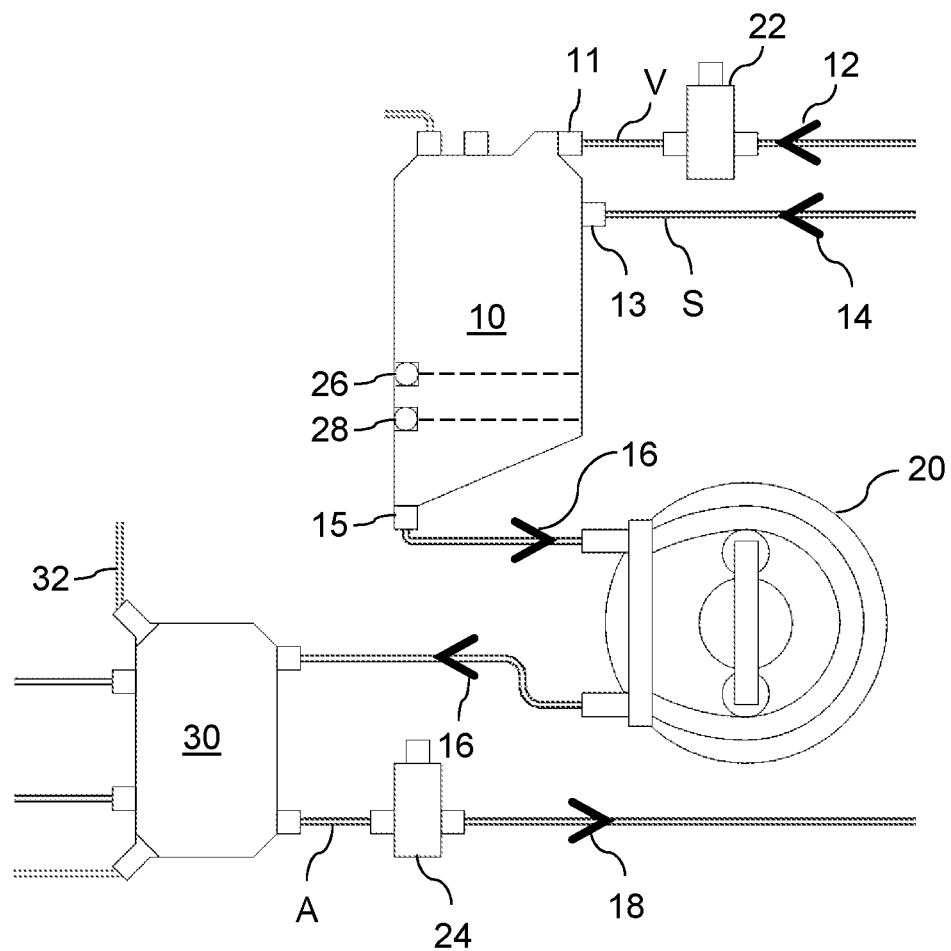
FIG. 1 shows a schematic arrangement of components of a control system for controlling the level of blood in a blood reservoir in accordance with embodiments of the present invention.

FIG. 1 shows a blood reservoir 10 installed as part of a perfusion system. The perfusion system provides extracorporeal blood circulation and blood oxygenation. A venous line V is provided upstream of the blood reservoir 10 to receive venous (oxygen-reduced) blood received from, for instance, a patient. In the venous line V, blood flows in a direction indicated by arrow 12 into the blood reservoir 10 via a reservoir inlet 11. The blood reservoir 10 is also called a "venous reservoir".

The blood reservoir 10 also receives blood from one or more other sources. FIG. 1 shows a salvage line S through which blood may be transported in a direction indicated by arrow 14 into the blood reservoir 10 via reservoir inlet 13.

Blood flow through the venous line V is generally steady, whereas blood flow through the salvage line S is intermittent, or less steady than the blood flow through the venous line V.

The blood reservoir 10 comprises a reservoir outlet 15 from which blood may be drawn by activation of a pump 20 located downstream of the blood reservoir 10 in a direction indicated by arrows 16. The blood is pumped through an oxygenator 30 in which the blood is supplied via supply line 32 with oxygenation gas to re-oxygenate the blood as arterial blood. The re-oxygenated, or arterial, blood leaves the oxygenator 30 via an arterial line A in the direction of arrow 18 and may then be supplied, for instance, to a patient. The arterial line constitutes an outgoing line through which outgoing (e.g., arterial) blood from the reservoir outlet 15 is transported at an outgoing (e.g., arterial) flow rate.

For the purpose of the present invention, it is assumed that the supply of venous blood into the blood reservoir 10 is dictated by circumstances and cannot be directly influenced. The flow rate of blood in the venous line V may depend on the rate at which blood was drained from a patient, and this may vary depending on the circumstances. The flow of blood through the salvage line S is infrequent, and may be sporadic and, at times, non-existent. Depending on the type of surgery, blood may be drawn from different locations simultaneously or at different times, leading to irregular blood flow into the blood reservoir 10. A venous flow sensor 22 is provided at the venous line V upstream of the blood reservoir 10. The venous flow sensor 22 is configured to measure the flow rate of venous blood entering the blood reservoir 10 via venous line V.

The flow rate of the arterial blood in the arterial line A can be assumed to be determined by the pump speed of the pump 20. I.e., if the pump 20 is operated at a higher pump speed, the flow rate of the arterial blood in the arterial line A increases correspondingly. If the pump 20 is operated at a lower pump speed, the flow rate of the arterial blood in the arterial line A decreases correspondingly. Stopping the pump 20 will stop the arterial blood flow. The flow rate of the arterial blood in the arterial line A may be affected by the oxygenator 30 due to its position downstream of the pump 20. An arterial flow sensor 24 is provided at the arterial line A downstream of the oxygenator 30. The arterial flow sensor 24 is configured to measure the flow rate of the arterial blood leaving the oxygenator 30.

Figure 2:
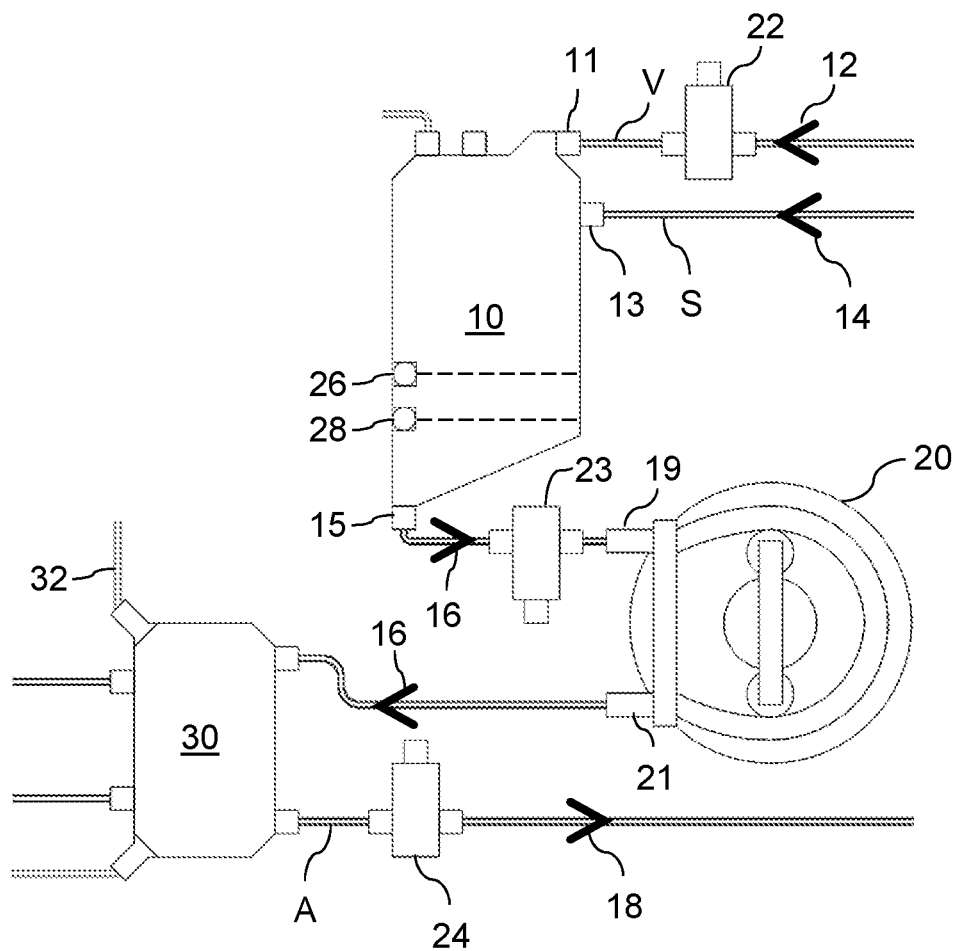
FIG. 2 shows a schematic arrangement of components of a control system for controlling the level of blood in a blood reservoir in accordance with embodiments of the present invention.

In FIG. 2, an embodiment is shown in which a main flow sensor 23 is provided in the main line downstream of the blood reservoir 10 and upstream of the pump 20. The blood flows via a pump inlet 19 through the pump 20 and exits the pump 20 via a blood outlet 21. The other components of FIG. 2 correspond to those shown in FIG. 1 and have the same numerals.

In the embodiment of FIG. 2, the main flow sensor 23 is provided in addition to the arterial flow sensor 24. Both the main flow sensor 23 and the arterial flow sensor 24 are outgoing flow sensors. The main flow sensor 23 may be provided as an alternative to the arterial flow sensor 24, i.e., there may be a single flow sensor upstream of the pump. It will be understood that, if provided upstream of the pump, an outgoing flow sensor may be positioned at the reservoir outlet 15, or at the pump inlet 19. It will be understood that, if provided downstream of the pump, an outgoing flow sensor may be positioned at the pump outlet 21.

As shown in both FIGS. 1 and 2, a blood level sensor system is provided to measure the blood level at a first blood level threshold 26 and at a second blood level threshold 28. It is understood that the level sensor system may be comprised of a single sensor of a type capable of measuring both blood level thresholds 26 and 28. The blood level sensor may comprise a plurality of sensors. One of the sensors may measure the first blood level threshold 26. One of the sensors may measure the second blood level threshold 28.

A controller (not shown) is provided to receive as inputs the venous flow rate and the arterial flow rate. The controller comprises decision logic to determine whether or not the arterial flow rate exceeds the venous flow rate. The decision logic permits the controller to issue a signal to the pump 20 to reduce the pump speed if the arterial flow rate, as measured by the main flow sensor 23 and/or the arterial flow sensor 24, exceeds the venous flow rate as measured by the venous flow sensor 22. Thereby, the decision logic provides a control of the pump 20 to prevent the arterial flow rate from exceeding the venous flow rate. This can be achieved by operating the pump 20 to maintain the arterial flow rate at and/or below the venous flow rate. If the outgoing flow sensors (main flow sensor 23 and arterial flow sensor 24) are in series, the decision logic is able to control the pump speed, e.g. to reduce the pump speed until the larger of the flow rates, as measured by the outgoing flow sensors, no longer exceeds the venous flow rate. This arrests a decrease in blood level in the blood reservoir 10.

If, for any reason, the blood level decreases to the level marked by the second blood level threshold 28, the controller is configured to issue a signal to the pump 20 to stop the pump 20. This stops the flow of blood out of the reservoir outlet 15.

By way of the described mechanism, it can be avoided that operation of the pump 20 causes the blood in the blood reservoir 10 to decrease to a level at which air may be sucked through reservoir outlet 15.

If, following a reducing or stopping the flow rate through the arterial line A, the blood supplied via venous line V and/or via salvage line S into the blood reservoir 10 leads to a blood level above the second blood level threshold 28 but below the first blood level threshold 26, the controller is configured to issue a signal to the pump 20 to circulate blood while preventing the arterial flow rate from exceeding the venous flow rate. If the blood level continues to increase in the blood reservoir 10 such that it exceeds the first blood level threshold 26, the controller is configured to operate the pump 20 independently of the venous flow rate.

Figure 3:
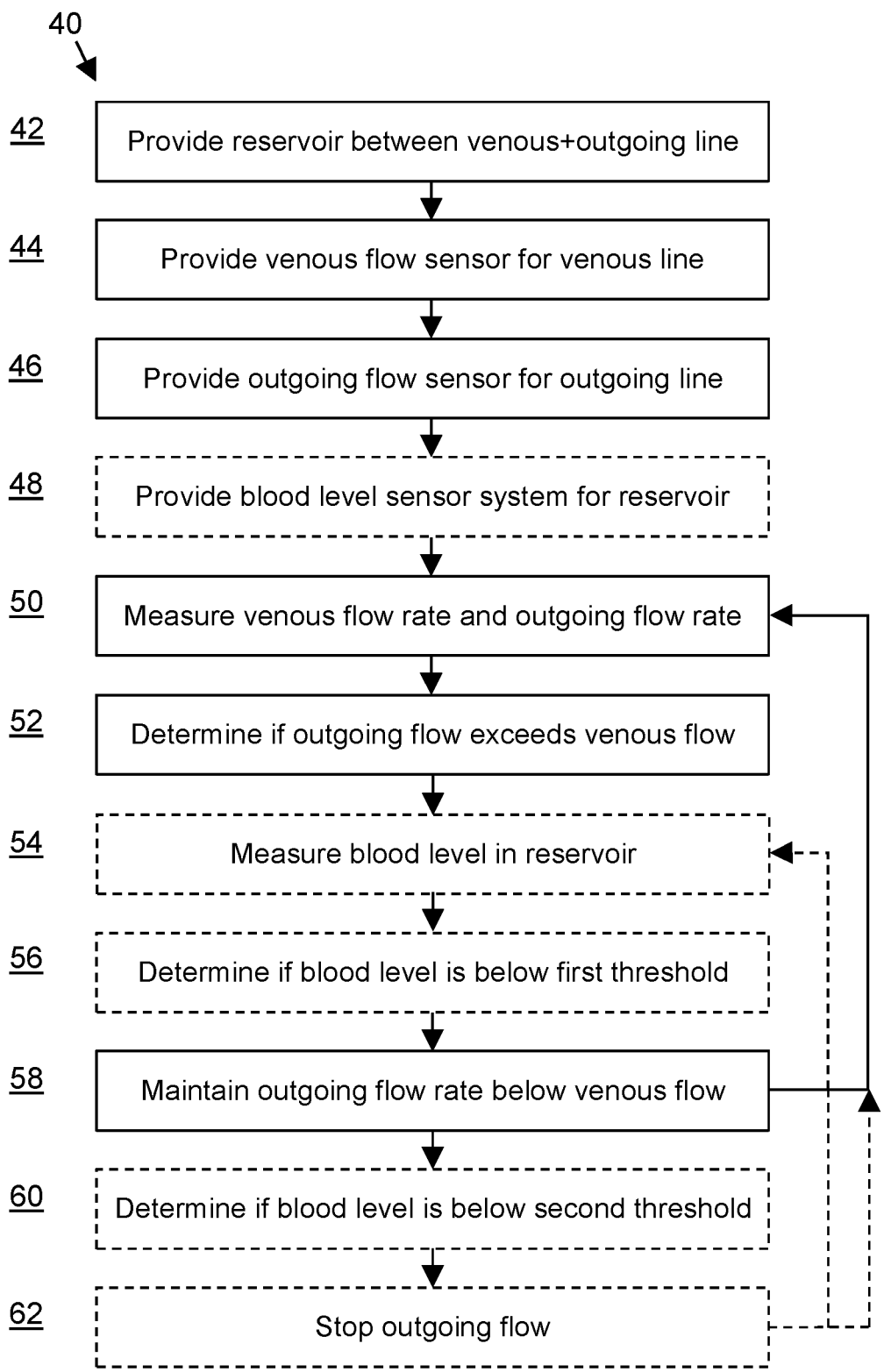
FIG. 3 shows steps of an exemplary sequence of method steps of a method for controlling the level of blood in a blood reservoir in accordance with embodiments of the invention.

FIG. 3 shows a sequence of steps of a method 40. The controller (not shown) may be configured to carry out some or all steps of the method 40.

In step 42, a blood reservoir is provided between a venous line and an outgoing (e.g., arterial) line. In step 44, a venous flow sensor is provided to measure the blood flow rate in the venous line. In step 46, an outgoing flow sensor is provided to measure the blood flow rate in the outgoing line. For example, if the outgoing line is a main line or an arterial line, the outgoing flow sensor may be constituted by a main flow sensor or an arterial flow sensor that is provided to measure the blood flow rate in the main line, or the arterial line, respectively. In an optional step 48, a blood level sensor system is provided to measure the level of blood in the blood reservoir.

In step 50, the venous flow rate is measured and the outgoing (e.g., arterial) flow rate is measured. In step 52, a determination is made as to whether or not the venous flow rate exceeds the outgoing flow rate. In an optional step 54, the blood level in the blood reservoir is measured. The optional step 54 is followed by an optional step 56 in which a determination is made whether or not the blood level is below a first threshold.

In step 58, the outgoing flow rate is prevented from exceeding the venous flow rate. The outgoing (e.g., arterial) flow rate may be maintained at and/or below the venous flow rate. Thereby, a decrease of the level of blood in the blood reservoir can be arrested. It is understood that the outgoing flow rate is influenced by controlling a pump circulating the blood through the outgoing line. In an embodiment of the method 40, step 58 is carried out if in optional steps 54 and 56 it was determined that the blood level is below the first blood threshold.

Step 54 may be followed by an optional step 60 in which a determination is made whether or not the blood level is below a second threshold. If the blood level is below the second threshold, then in step 62 the outgoing flow is stopped. It is understood that the outgoing flow is stopped by stopping operation of the pump provided for circulating the blood through the outgoing line.

It will be understood that step 56 and step 60 may be carried out concurrently, or that step 56 may be carried out only if the determination of step 60 yields that blood level is above the second threshold. For instance, the decision logic may conclude that if the blood level is below the second blood threshold, it is therefore also below the first blood threshold. The decision logic may then carry out, as appropriate, either step 58 to maintain the outgoing flow rate below the venous flow rate or step 62 to stop the outgoing flow. The outgoing flow may be stopped gradually, e.g., to avoid blood-inertia induced pressure spikes.

Step 50 is repeated. In embodiments comprising optional step 54, step 54 is repeated. Thereby, a closed loop control mechanism is provided. In an embodiment, the outgoing flow rate may be controlled by the pump independently of the venous flow rate if in step 56 it is determined that the blood level is not below the first threshold.

Although the description herein refers to a blood level sensor system, a first blood level threshold 26 and at a second blood level threshold 28, the present invention may be embodied in control systems that determine a quantity of blood in the blood reservoir 10 other than by blood level. For instance, instead of a blood level, the blood volume or blood weight (mass) may be measured by the sensor system. The sensor system may be constituted by a single sensor capable of measuring one or more blood quantity thresholds. The sensor system may comprise two or more individual sensors, one each for measuring a blood quantity threshold.

The Applicant of the present invention has appreciated that a suitably reliable feedback loop to prevent ingress of air bubbles via the reservoir outlet 15 can be achieved by positioning a venous flow sensor 22 in the venous line V. FIG. 1 shows one venous line V and one salvage line S. It will be understood that any number of connections may feed blood into the blood reservoir 10. Although one venous flow sensor 22 is shown, embodiments may comprise multiple venous flow sensors 22, one each for a line feeding blood into the reservoir. In that case, the venous flow rate may be understood as the combined flow rate as determined by the multiple venous flow sensors.

Figure 4:
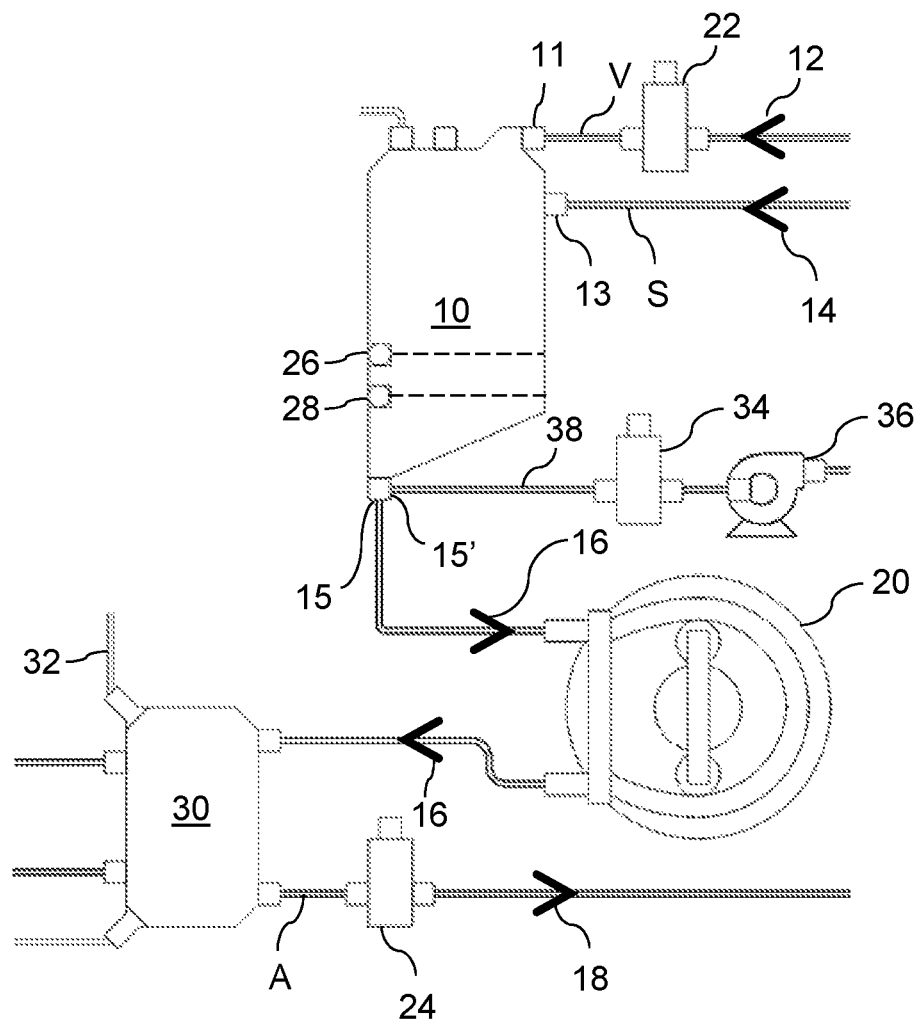
FIG. 4 show a schematic arrangement of components of a control system for controlling the level of blood in a blood reservoir in accordance with additional embodiments of the present invention.

Likewise, as seen in FIG. 4, embodiments may comprise multiple outgoing flow sensors 24, 34. For instance, where the specification refers to an outgoing flow sensor positioned at the reservoir outlet, in systems with multiple reservoir outlets, an outgoing flow sensor may be provided at each of the multiple reservoir outlets.

Although the present specification refers to a pump to indicate the main pressure pump, there may be two or more pumps 20, 36, e.g., as part of a pump arrangement. For instance, a first pump 20 may, as the main pressure pump, allow blood to be drawn from a first reservoir outlet 15 through a first outgoing line, and a second pump 36 may, in parallel to the first pump 20, allow blood to be drawn directly from the same blood reservoir 10 via a second reservoir outlet 15' through a second outgoing line 38. For instance, such a second pump may provide a cardioplegia line 38 for the administration of cardioplegic (heart-arresting) agent.

In such arrangements, it will be understood that the controller will be configured to control the combined pump throughput of all pumps in the pump arrangement in order to arrest a decrease of blood in the blood reservoir. A plurality of outgoing flow sensors 24, 34 may be provided, for instance one per outgoing line. Flow sensors in different outgoing lines may be regarded as parallel flow sensors 24, 34. The controller may comprise decision logic to modulate the flow rate for each of the pumps to prevent the cumulative outgoing flow rates from exceeding the venous flow rate.

The controller may reduce the flow of one or more second pumps before modulating the flow through the first pump.

The controller may reduce the flow of one or more second pumps in proportion to the first pump.

The controller may use hierarchical decision logic to reduce and/or stop the decrease of blood in the blood reservoir. Using the example of a cumulative outgoing flow of a first pump and a second pump, the decision logic may initially reduce the flow via the second pump to a minimum value above zero, without modulating the first pump. This will permit reduced flow via the second pump. If a further reduction of the cumulative outgoing flow rate is required, for instance because there was no flow via the second pump at that moment in time, the decision logic may reduce the flow via the first pump to a minimum value above zero, such that all flows are reduced to prevent the cumulative outgoing flow rate from exceeding the venous flow rate. If a further reduction of the cumulative outgoing flow is required, the decision logic may stop the second pump. This will permit flow via the first pump only. If it is necessary to stop the cumulative (i.e., any) outgoing flow, the decision logic will stop all pumps (both the first pump and the second pump).

The blood in the outgoing line may not necessarily be oxygenated or "arterialised" unless it passed an oxygenator. For instance, outgoing blood may be used in the course of left-heart bypass surgery, in which case this is not passed through an oxygenator. Blood may be diverted upstream of the oxygenator for purge purposes. Thus, when the present specification refers to an arterial line with an arterial flow, this is to be understood as an example of an outgoing line with an outgoing flow.

The invention claimed is:

1. A control system for controlling a quantity of blood in a blood reservoir of a perfusion system in which the blood reservoir is supplied through a venous line and a pump is configured to circulate blood out of the blood reservoir through an outgoing line, the control system comprising:
   a venous flow sensor configured to measure a venous flow rate of blood in the venous line;
   an outgoing flow sensor configured to measure an outgoing flow rate of blood in the outgoing line;
   a blood quantity sensor system configured to generate a blood quantity output indicative of a quantity of blood in the blood reservoir; and
   a controller, the controller configured to receive as inputs the measured venous flow rate, the measured outgoing flow rate and the blood quantity output, and to determine whether the blood quantity output is below a first blood quantity threshold,
   wherein the controller comprises decision logic responsive to whether the measured outgoing flow rate exceeds the measured venous flow rate, wherein the decision logic is configured to:
   (a) only while the quantity of blood is below the first blood quantity threshold, cause the controller to perform closed loop control of the pump, based on the measured outgoing flow rate and the measured venous flow rate, to prevent the outgoing flow rate from exceeding the venous flow rate so as to arrest a decrease of blood in the blood reservoir; and
   (b) while the quantity of blood is above the first blood quantity threshold, cause the controller to control the pump independently of the measured venous flow rate.

2. A control system according to claim 1, wherein the outgoing line is an arterial line, and wherein the outgoing flow sensor is an arterial flow sensor configured to measure as the outgoing flow rate an arterial flow rate of blood in the arterial line, to prevent the arterial flow rate from exceeding the venous flow rate.

3. The control system according claim 2, wherein the controller is configured to determine whether the blood quantity output is below a second blood quantity threshold, and to stop the pump to stop the outgoing flow while the quantity of blood is below the second blood quantity threshold.

4. The control system according to claim 3, wherein the blood quantity sensor system comprises a blood quantity sensor capable of monitoring the first blood quantity threshold and the second blood quantity threshold.

5. The control system according to claim 3, wherein the blood quantity sensor system comprises a first blood quantity sensor for monitoring the first blood quantity threshold and a second blood quantity sensor for monitoring the second blood quantity threshold.

6. The control system according to claim 1, wherein the blood quantity sensor system is configured to measure the quantity of blood based on at least one selected from the group consisting of: the level of blood in the blood reservoir, the volume of blood in the blood reservoir, and the mass of blood in the blood reservoir.

7. The control system according to claim 1, wherein the blood reservoir is further supplied by at least one salvage line, and wherein a blood flow through the at least one salvage line is not considered in the determination by the controller as to whether or not the measured outgoing flow rate exceeds the measured venous flow rate.

8. The control system according to claim 1, comprising a plurality of outgoing flow sensors, each outgoing flow sensor to measure an outgoing flow rate at a different location of the outgoing line.

9. The control system according to claim 8, wherein the plurality of outgoing flow sensors is in series and the controller is configured to receive as inputs the measured outgoing flow rates of the outgoing flow sensors in series, and wherein the controller is configured to issue the signal to control the pump if any of the measured outgoing flow rates exceeds the measured venous flow rate.

10. The control system according to claim 8, wherein the plurality of outgoing flow sensors is in parallel and the controller is configured to receive as inputs the measured outgoing flow rates of the parallel outgoing flow sensors, to determine a cumulative outgoing flow rate as the sum of the measured outgoing flow rates, and wherein the controller is configured to issue the signal to control the pump if the cumulative outgoing flow rate exceeds the measured venous flow rate.

11. A method of controlling a quantity of blood in a blood reservoir, the blood reservoir for use in a perfusion system in which the blood reservoir is supplied through a venous line and a pump is configured to circulate blood out of the blood reservoir through an outgoing line, the method comprising the steps of:
   using a venous flow sensor to measure a venous flow rate of blood in the venous line;
   using an outgoing flow sensor to measure an outgoing flow rate of blood in the outgoing line;
   using a sensor to measure a blood quantity output indicative of a quantity of blood in the blood reservoir;
   determining whether the blood quantity output is below a first blood quantity threshold;
   determining whether or not the measured outgoing flow rate exceeds the measured venous flow rate; and
   responsive to determining that the measured outgoing flow rate exceeds the measured venous flow rate:
   (a) only while the blood quantity output is below the first blood quantity threshold, controlling the pump to perform closed loop control based on the measured outgoing flow rate and the measured venous flow rate, so as to prevent the outgoing flow rate from exceeding the venous flow rate so as to arrest a decrease in blood in the blood reservoir; and
   (b) while the quantity of blood is above the first blood quantity threshold, controlling the pump independently of the measured venous flow rate.

12. The method according to claim 11, wherein the outgoing line is an arterial line and the outgoing flow sensor is an arterial flow sensor, and wherein the method comprises using the arterial flow sensor to measure as the outgoing flow rate an arterial flow rate of blood in the arterial line, determining whether or not the measured arterial flow rate exceeds the measured venous flow rate, and operating the pump so as to prevent the arterial flow rate from exceeding the venous flow rate.

13. The method according to claim 12, further comprising the step of controlling the pump independently of the measured venous flow rate if the quantity of blood is above the first blood quantity threshold.

14. The method according to claim 11, further comprising the steps of:
   determining whether the quantity of blood is below a second blood quantity threshold, and
   stopping the pump to stop the outgoing flow while the quantity of blood is below the second blood quantity threshold.

15. The method according to claim 11, further comprising using a plurality of outgoing flow sensors, and using each outgoing flow sensor to measure an outgoing flow rate at a different location of the outgoing line.

16. The method according to claim 15, further comprising positioning the plurality of outgoing flow sensors in series, determining the outgoing flow rates of each of the outgoing flow sensors in series, and operating the pump if any of the outgoing flow rates exceeds the measured venous flow rate.

17. The method according to claim 15, further comprising positioning the plurality of outgoing flow sensors in parallel, determining a cumulative outgoing flow rate as the sum of the outgoing flow rates, and operating the pump if the cumulative outgoing flow rate exceeds the measured venous flow rate.

* * * * *